United States Patent [19]
Yu

[11] Patent Number: 5,286,201
[45] Date of Patent: Feb. 15, 1994

[54] AIR DRYER DEVICE FOR A DENTAL 3-WAY SYRINGE

[76] Inventor: Chih-Ming Yu, No. 28, Kung Kuan St., Wen Shan Area, Taipei, Taiwan

[21] Appl. No.: 79,035
[22] Filed: Jun. 21, 1993
[51] Int. Cl.$^5$ .......................................... A61G 17/02
[52] U.S. Cl. ...................................................... 433/80
[58] Field of Search ........................................ 433/80

[56] References Cited
U.S. PATENT DOCUMENTS 1,874,917 8/1932 Dannequin ............................ 433/80
4,741,697 5/1988 Herbison ............................... 433/80
4,950,159 8/1990 Hansen ................................. 433/80

Primary Examiner—John J. Wilson

[57] ABSTRACT

An air dryer device including a tapered cylindrical casing consisting of five sections and fastened to a dental 3-way syringe for the holding of the hand, and an air dryer unit fastened inside the tapered cylindrical casing to remove moisture from the air being compressed to the dental 3-way syringe, the air dryer unit consisting of a layer of activated aluminum particles, a layer of activated carbon, and an air filter board respectively separated by wire gauzes.

1 Claim, 5 Drawing Sheets

AIR DRYER DEVICE FOR A DENTAL 3-WAY SYRINGE

BACKGROUND OF THE INVENTION

The present invention relates to an air dryer device detachably fastened to a dental 3-way syringe to dry the air being compressed to the dental 3-way syringe and simultaneously to serve as the handle of the dental 3-way syringe for the holding of the hand.

The dry air ejected through the tip of a dental 3-way syringe is commonly obtained from a high-pressure air supply system, which is generally comprised of an air compressor, an air aftercooler, and an air filter. This structure of air supply system can not effectively remove oil, water, oil vapor, water vapor, etc. from the air being compressed to the dental 3-way syringe. Therefore, an additional air dryer device is needed. There are two types of air dryer devices being commonly used in dental clinics, namely, the absorptive type and the frozen type. A frozen type air dryer device is easy to maintain. However, it is difficult to obtain a dry air of very low dew point through a frozen type air dryer device. An absorptive type air dryer device uses a desicant to absorb moisture from the air passing through. The desicant must be regularly dried by pumping hot and dry air through it so that it can be repeatedly used again and again. However, an absorptive type air dryer device is expensive and must be regularly maintained through a complicated procedure. Because it is not necessary to dry the air being compressed for driving a pneumatic type dental instrument, for example: high-speed handpieces, it is not economic to constantly incorporate an air dryer device in the high-pressure air supply system. In general, regular air dryer devices have drawbacks as follows:

1) They are commonly expensive, and will increase the cost of medical treatment.
2) Absorptive type air dryers are difficult and expensive to maintain.
3) They are commonly heavy and need much installation space.
4) It is not economic to use the compressed air being treated through an expensive air dryer device simply for driving a pneumatic type dental instrument.

SUMMARY OF THE INVENTION

The present invention has been accomplished under the aforesaid circumstances. It is therefore the principal object of the present invention to provide an air dryer device for a dental 3-way syringe which is simple in structure and effective in function. It is another object of the present invention to provide an air dryer device for a dental 3-way syringe which can be conveniently attached to a dental 3-way syringe for drying the air being compressed to the dental 3-way syringe and simultaneously for serving as the handle of the dental 3-way syringe for the holding of the hand. It is still another object of the present invention to provide an air dryer for a dental 3-way syringe which is inexpensive to manufacture. It is still another object of the present invention to provide an air dryer for a dental 3-way syringe which is easy of use. It is still another object of the present invention to provide an air dryer for a dental 3-way syringe which is easy to maintain.

According to the preferred embodiment of the present invention, the air dryer device is comprised of an air dryer unit fastened inside a tapered cylindrical casing. The casing is made for holding by the hand, and detachably connected to a dental 3-way syringe through screw joints. The air dryer unit comprises a layer of activated aluminum particles, a layer of activated carbon, and an air filter board, respectively separated by wire gauzes. Two air circulation holes are made on the casing at two opposite ends which are normally closed, and which are opened for passing a dry and hot air to remove moisture from the air dryer unit during a maintenance work.

DETAILED DESCRIPTION OF THE PREFERRED EMBODIMENT

Figure 1:
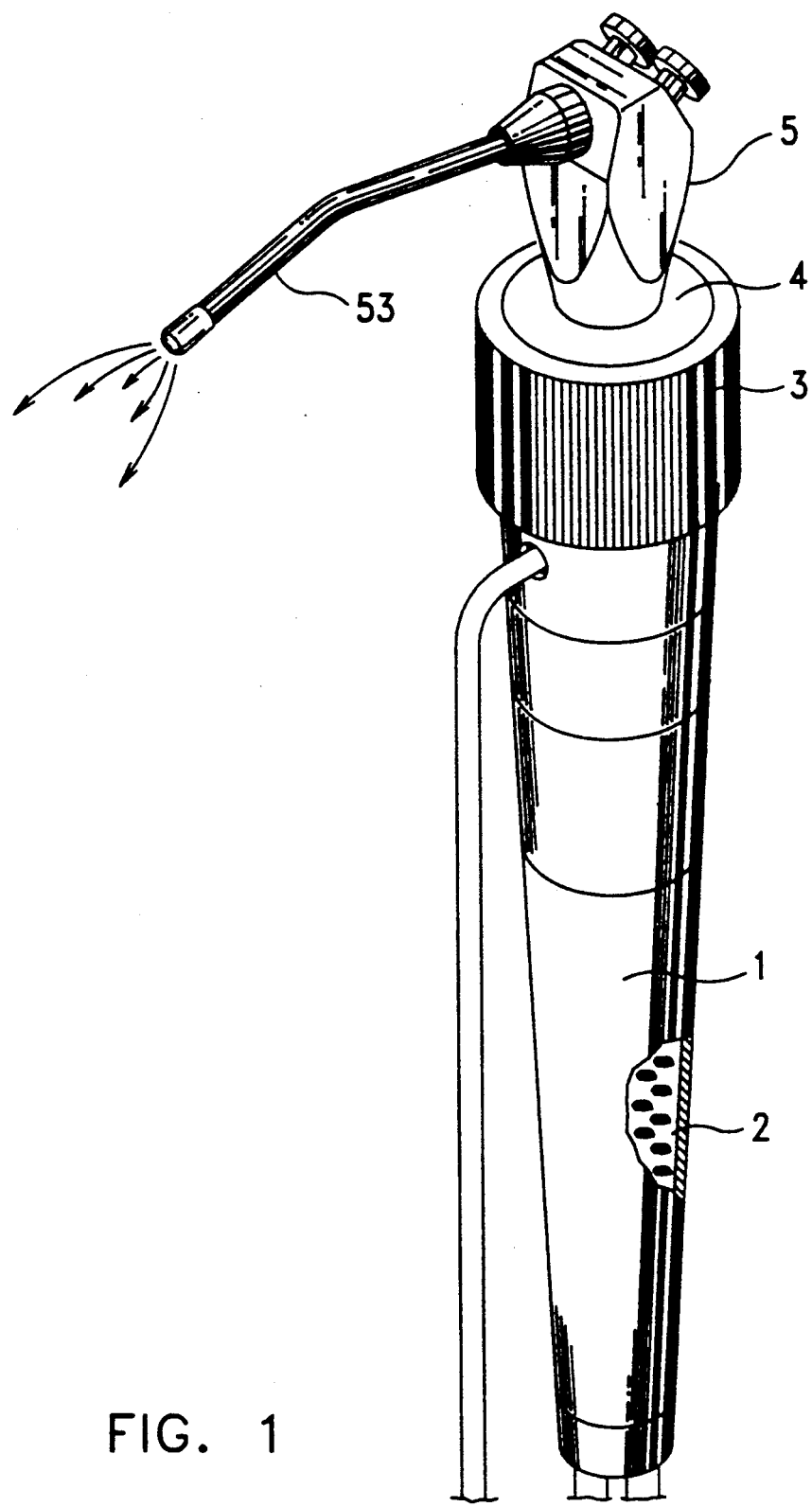
FIG. 1 is a perspective installed view showing the preferred embodiment of the air dryer device connected to a dental 3-way syringe.
Figure 2:
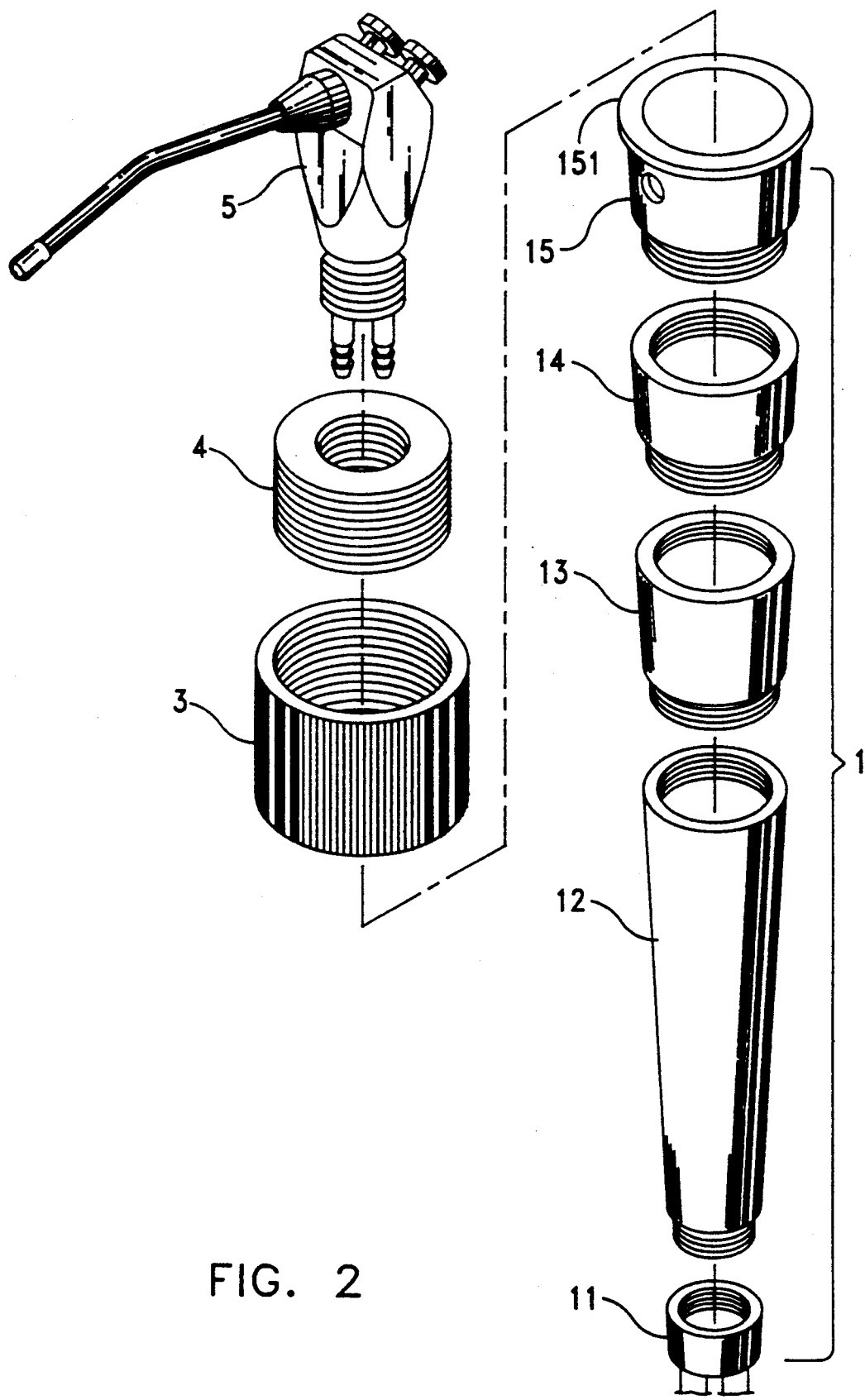
FIG. 2 is an exploded view of the tapered cylindrical casing of the air dryer device.

Referring to FIGS. 1 and 2, an air dryer device according to the preferred embodiment is generally comprised of a tapered cylindrical casing 1 connected to a dental 3-way syringe 5 by a screw connector 4 and a screw socket 3, and an air dryer unit 2 fastened inside the tapered cylindrical casing 1.

Figure 3:
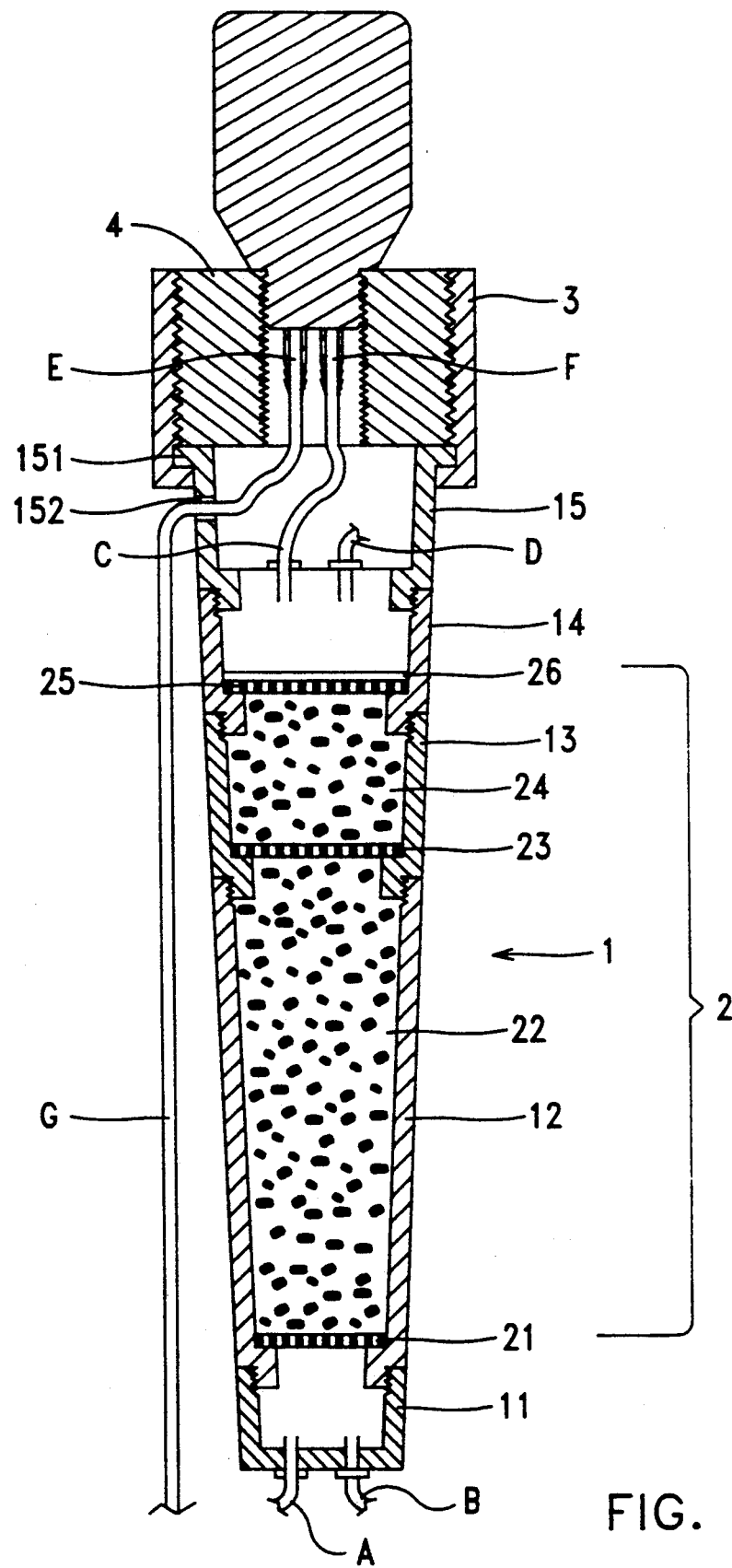
FIG. 3 is a longitudinal sectional view showing the arrangement of the air dryer unit within the tapered cylindrical casing.

Referring to FIG. 3 and FIG. 2 again, the tapered cylindrical casing 1 is made gradually smaller toward one end, and comprised of five cylindrical sections, namely, the first cylindrical section 11 (the one having the relatively smallest outer diameter), the second cylindrical section 12, the third cylindrical section 13, the fourth cylindrical section 14, and the fifth cylindrical section 15 (the one having the relatively biggest outer diameter). The five cylindrical sections of the tapered cylindrical casing 1 are properly connected in series through respective screw joints. The first cylindrical section 11 of the tapered cylindrical casing 1 has two holes on the blocked bottom edge thereof, namely, the air intake hole A and the air circulation hole B. The air outlet hole C of the fifth cylindrical section 15 of the tapered cylindrical casing 1 is connected to the air intake port F of the dental 3-way syringe 5. The fifth cylindrical section 15 of the tapered cylindrical casing 1 has two holes on the blocked bottom edge thereof, namely, the air outlet hole C and the air circulation hole D. The air circulation holes B;D are normally closed, which will be opened only when a maintenance work is to be done. The screw socket 3 has an inward annular flange (not shown) at the bottom surrounding. The fifth cylindrical section 15 has a horizontal outward flange 151 at the top in diameter relatively bigger than the hole defined within the inward annular flange of the screw socket 3 but relatively smaller than the inner diameter of the screw socket 3. Therefore, the fifth cylindrical section 15 can be connected to the screw socket 3 by inserting it through the screw socket 3 from the top to let the horizontal outward flange 151 of the fifth cylindrical section 15 be engaged with the inward annular flange of the screw socket 3. The screw connector 4 is fastened to the bottom end of the dental 3-way syringe 5 through a screw joint, and then the screw socket 3 is fastened to the screw connector 4 through a screw joint to hold the tapered cylindrical casing 1 to the dental 3-way syringe. The fifth cylindrical section 15 of the tapered cylindrical casing 1 further comprises a through hole 152 through the peripheral wall thereof through which a water supply tubing G is inserted and then connected to the water intake port E of the dental 3-way syringe 5. The air dryer unit 2 comprises a lower wire gauze 21 fastened between the first cylindrical section 11 and second cylindrical section 12 of the tapered cylindrical casing 1, an intermediate wire gauze 23 fastened between the second cylindrical section 12 and third cylindrical section 13 of the tapered cylindrical casing 1, an upper wire gauze 25 fastened between the third cylindrical section 13 and fourth cylindrical section 14 of the tapered cylindrical casing 1, a layer of activated aluminum particles 22 filled in the second cylindrical section 12 of the tapered cylindrical casing 1 between the lower wire gauze 21 and the intermediate wire gauze 23, a layer of activated carbon 24 filled in the third cylindrical section 13 of the tapered cylindrical casing 1 between the intermediate wire gauze 23 and the upper wire gauze 25, and an air filter board 26 fastened inside the fourth cylindrical section 14 of the tapered cylindrical casing 1 and covered over the upper wire gauze 25.

Figure 4:
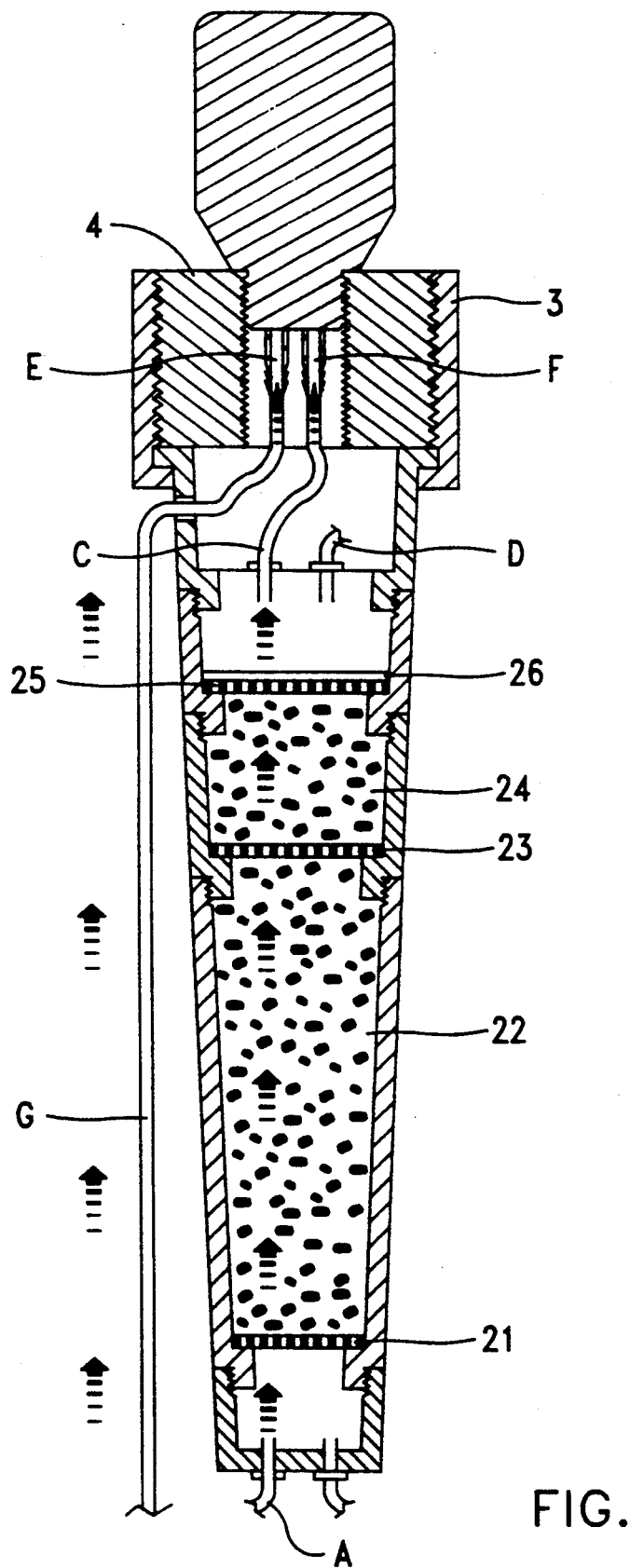
FIG. 4 is similar to FIG. 3 but showing a current of air flowing through the air dryer unit to the air intake port of the dental 3-way syringe and a current of water flowing through the water supply tubing to the water intake port of the dental 3-way syringe.

Referring to FIG. 4, when a flow of compressed air is pumped into the air intake hole A, the current of compressed air immediately flows through the layer of activated aluminum particles 22. While passing through the activated aluminum particles 22, moisture is immediately removed from the current of air by the aluminum particles. As the current of compressed air flows continuously upwards through the layer of activated carbon 24, organic solvent is immediately removed from the current of compressed air by the activated carbon. After passing through the layer of activated carbon 24, the current of compressed air is immediately filtrated through the air filter board 26. After the treatment of the air dryer unit 2, the current of compressed air is guided through the air outlet hole C to the air intake port F, and then ejected out of the dental 3-way syringe 5 through a tip 53 (see also FIG. 1). At the same time, a flow of water may be pumped into the water intake port E of the dental 3-way syringe 5 through the water supply tubing G.

Figure 5:
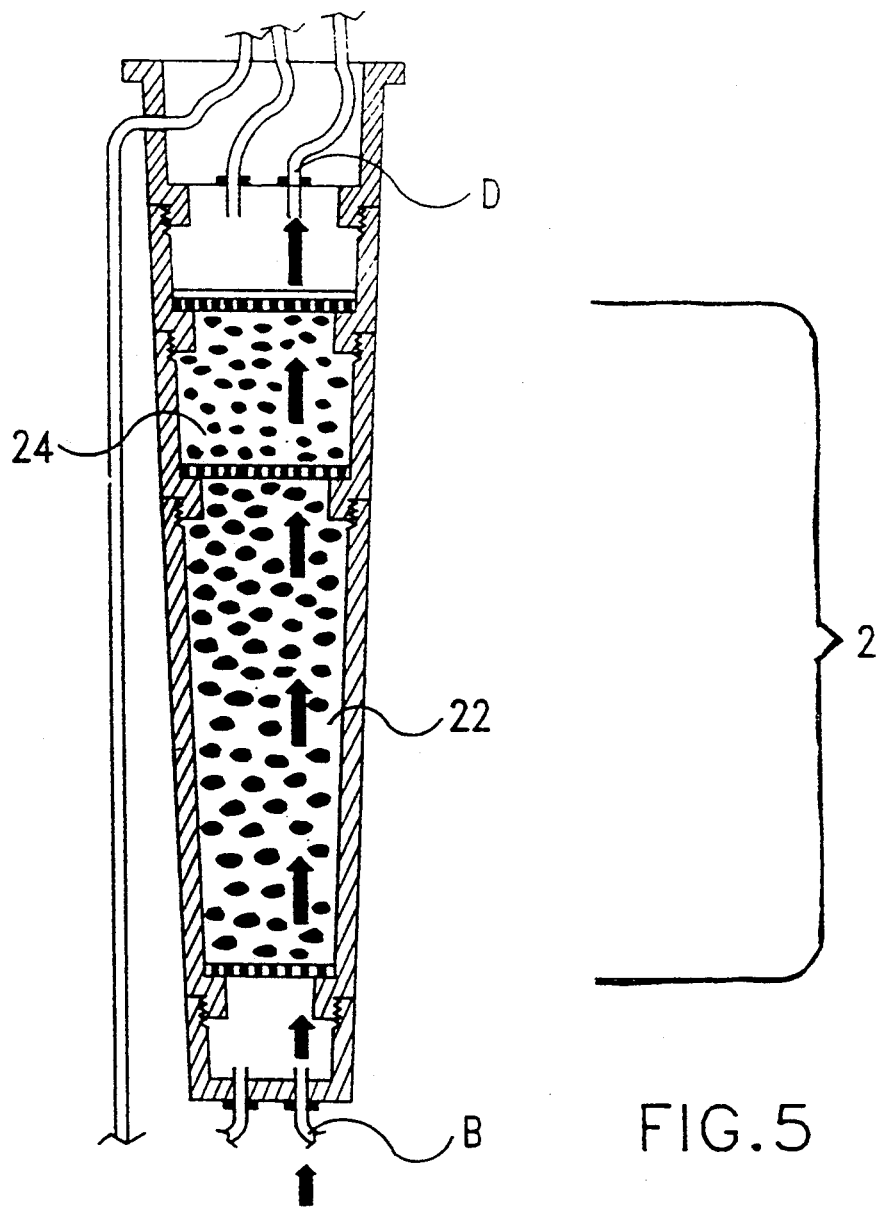
FIG. 5 is similar to FIG. 3 but showing a current of dry and hot air flowing through the air dryer unit to remove moisture away from the layer of activated aluminum particles and the layer of activated carbon.

Referring to FIG. 5, the maintenance of the air dryer device is done by removing the screw socket 3 from the dental 3-way syringe 5 then opening the air circulation holes B;D and then pumping a current of dry and hot air into the air circulation hole B on the first cylindrical section 11 of the tapered cylindrical casing 1 to carry moisture and organic solvent from the layer of activated aluminum particles 22 and the layer of activated carbon 24.

What is claimed is:

1. An air dryer device comprising a tapered cylindrical casing detachably connected to a dental 3-way syringe by a screw connector and a screw socket, and an air dryer unit fastened inside said tapered cylindrical casing for drying air passing through, said cylindrical casing comprising a first section, a second section, a third section, a fourth section, and a fifth section respectively connected in series through screw joints, said first section being disposed at one end, said fifth section being disposed at an opposite end and connected to said screw connector by said screw socket, said first section comprising a first air intake hole and a second air intake hole respectively made through a blocked bottom edge thereof, said fifth section comprising a first air outlet hole and a second air outlet hole respectively made through a blocked bottom edge thereof and a side hole on a peripheral wall thereof, the first air outlet hole of said fifth section being connected to the air intake port of the dental 3-way syringe by a tubing, the side hole on said fifth section being for inserting a water supply tubing for allowing the water supply tubing to be connected to the water intake port of the dental 3-way syringe, the air dryer unit comprising a lower wire gauze fastened between said first section and said second section, an intermediate wire gauze fastened between said second section and said third section, an upper wire gauze fastened between said third section, and said fourth section, a layer of activated aluminum particles filled in said second section between said lower wire gauze and said intermediate wire gauze, a layer of activated carbon filled in said third section between said intermediate wire gauze and said upper wire gauze, and an air filter board fastened inside said fourth section and covered over said upper wire gauze, said second air intake hole and said second air outlet hole being respectively sealed during the operation of the air dryer device, or opened for pumping a current of dry and hot air through said air dryer unit to remove moisture away as said tapered cylindrical casing is detached from the dental 3-way syringe.

* * * * *